United States Patent
Kawabata et al.

(10) Patent No.: US 10,856,649 B2
(45) Date of Patent: Dec. 8, 2020

(54) TOOTHBRUSH

(71) Applicant: OMRON HEALTHCARE Co., Ltd., Kyoto (JP)

(72) Inventors: Yasuhiro Kawabata, Kyoto (JP); Hideyuki Yamashita, Kyoto (JP); Kotaro Kitajo, Kyoto (JP); Hideaki Yoshida, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 190 days.

(21) Appl. No.: 16/167,588

(22) Filed: Oct. 23, 2018

(65) Prior Publication Data

US 2019/0053614 A1 Feb. 21, 2019

Related U.S. Application Data

(63) Continuation of application No. PCT/JP2017/016765, filed on Apr. 27, 2017.

(30) Foreign Application Priority Data

May 11, 2016 (JP) .................................. 2016-095278

(51) Int. Cl.
*A61C 17/22* (2006.01)
*A61C 17/34* (2006.01)
(Continued)

(52) U.S. Cl.
CPC ............ *A46B 15/0036* (2013.01); *A46B 9/04* (2013.01); *A46B 15/00* (2013.01); *A61C 17/00* (2013.01);
(Continued)

(58) Field of Classification Search
CPC ....... A61C 17/22; A61C 17/224; A46B 15/00; A46B 15/0088
See application file for complete search history.

(56) References Cited

U.S. PATENT DOCUMENTS

| 5,894,620 A * | 4/1999 | Polaert | A61B 5/0088 15/22.1 |
|---|---|---|---|
| 6,862,771 B1 | 3/2005 | Muller | |
| 2014/0199651 A1 * | 7/2014 | Adachi | A61C 17/221 433/27 |

FOREIGN PATENT DOCUMENTS

| CN | 101606783 A | 12/2009 |
|---|---|---|
| CN | 103764063 A | 4/2014 |

(Continued)

OTHER PUBLICATIONS

Office Action dated Jan. 2, 2020 in corresponding Chinese Application No. 201780029020.3; 15 pages including English-language translation.

(Continued)

*Primary Examiner* — Michael D Jennings
(74) *Attorney, Agent, or Firm* — Maier & Maier, PLLC (57) ABSTRACT

A toothbrush includes a main body that includes a head portion with a bristle raising surface on which bristles are provided in a standing manner, a grip portion, and a neck portion. A light emission portion that emits light through a specific region of the bristle raising surface toward a tooth surface and a light reception portion that receives radiated light from the tooth surface resulting from the light, through the specific region, are provided inside of the main body. It is determined whether or not there is dental plaque on the tooth surface based on the output of the light reception portion. A light reception and condensing portion that condenses the radiated light from the tooth surface toward the light reception surface of the light reception portion is arranged in the housing portion forming the specific region.

5 Claims, 8 Drawing Sheets

(51) Int. Cl.
    *A46B 15/00*   (2006.01)
    *A46B 9/04*    (2006.01)
    *A61C 17/00*   (2006.01)

(52) U.S. Cl.
    CPC .......... *A61C 17/22* (2013.01); *A46B 15/0044* (2013.01); *A46B 2200/1066* (2013.01)

(56) References Cited

FOREIGN PATENT DOCUMENTS

| | | | |
|---|---|---|---|
| JP | 2002-522102 | A | 7/2002 |
| JP | 2008-532619 | A | 8/2008 |
| JP | 2013-531674 | A | 8/2013 |
| KR | 20110051790 | A | 5/2011 |

OTHER PUBLICATIONS

International Search Report and Written Opinion dated Jun. 6, 2017 of corresponding International Application No. PCT/JP2017/016765; 6 pgs.

Office Action dated Jul. 29, 2020, in corresponding Chinese Application No. 201780029020.3, 18 pages.

Japanese Office Action dated Jun. 16, 2020, in connection with corresponding JP Application No. 2016-095278 (7 pp., including machine-generated English translation).

\* cited by examiner

TOOTHBRUSH

FIELD

The present invention relates to a toothbrush, and more specifically relates to a toothbrush including a light emission portion that emits light to a tooth surface in order to determine whether or not there is dental plaque on the tooth surface, and a light reception portion that receives radiated light from the tooth surface.

BACKGROUND

Conventionally, as this kind of toothbrush, as disclosed in Patent Document 1 (JP 2008-532619A), a toothbrush has been known which includes a head on which bristles are provided in a standing manner, an approximately central region of a bristle raising surface (bristle holding surface) of the head being provided with a light emission element for emitting light to the tooth surface (see FIG. 4, for example, in Patent Document 1). A light emission surface (a surface of transparent resin) of the light emission element is hemispherical in order to increase the light condensing efficiency, and is arranged protruding from the bristle raising surface to the outside.

PATENT LITERATURE

Patent Document 1: JP 2008-532619A
Patent Document 2: JP 2002-522102A

SUMMARY

However, with the toothbrush of Patent Document 1, the light emission surface protrudes in a hemispherical shape from the bristle raising surface of the head, and therefore during use, water droplets are more likely to attach to the periphery of the hemispherical light emission surface. If a water droplet (having a refractivity of about 1.3) attaches to the periphery of the light emission surface, the refractivity difference between the transparent resin (having a refractivity of about 1.5) forming the light exit surface and the periphery (water droplets) will reduce to about 0.2, the lens effect will mostly be lost, and the light condensing efficiency will decrease, which is problematic. This circumstance is thought to be similar also in the case where a light reception element for receiving radiated light from a tooth surface and a convex light condensing lens protruding from the bristle raising surface are provided in a specific region of the bristle raising surface of the head.

In view of this, the present invention aims to provide a toothbrush that includes a light condensing portion in a specific region of a bristle raising surface of a head portion, and can stably maintain a light condensing efficiency of the light condensing portion.

In order to solve the foregoing problem, a toothbrush of the present invention includes:

a main body including a head portion with a bristle raising surface on which bristles are provided in a standing manner, a grip portion to be gripped with a hand, and a neck portion that joins the head portion and the grip portion, a light emission portion configured to emit light through a specific region of the bristle raising surface toward a tooth surface, and a light reception portion configured to receive radiated light from the tooth surface resulting from the light, through the specific region, being included inside of the main body, wherein it is determined whether or not there is dental plaque on the tooth surface based on an output of the light reception portion, a light reception and condensing portion including a lens configured to condense the radiated light from the tooth surface toward a light reception surface of the light reception portion is arranged in a housing portion forming the specific region, and a region of the bristle raising surface of the head portion that includes the specific region and is larger than the specific region is flat.

Here, "inner portion of the main body" indicates the inner portion of the head portion, the neck portion, or the grip portion.

The "housing portion" forming the specific region indicates a portion of the outer wall (outer housing portion) of the head portion corresponding to the specific region.

The "region of the bristle raising surface that includes the specific region and is larger than the specific region being flat" means that the region that influences the light condensing efficiency of the light reception and condensing portion is flat. The entirety of the bristle raising surface, including the region of the bristle raising surface that surrounds the bristles, is flat.

With the toothbrush of the present invention, the light emission portion emits light through the specific region of the bristle raising surface to the tooth surface. The light reception portion receives the radiated light from the tooth surface resulting from the light, through the specific region, or in other words, the light reception portion receives the radiated light through the light reception and condensing portion. It is determined whether or not there is dental plaque on the tooth surface using a known procedure of detecting fluorescent light unique to dental plaque, which is disclosed in Patent Document 2 (JP 2002-522102A), for example. Here, with this toothbrush, the light reception and condensing portion that includes a lens and is arranged in the housing portion of the specific region condenses the radiated light from the tooth surface toward the light reception surface of the light reception portion. Accordingly, the output of the light reception portion increases, and as a result, it is possible to improve the accuracy of determining whether or not there is dental plaque on the tooth surface. Moreover, with this toothbrush, the region of the bristle raising surface of the head portion that includes at least the specific region and is larger than the specific region is flat. For this reason, during use, water droplets are not likely to attach to the light reception and condensing portion and its periphery. Accordingly, the light condensing efficiency of the light reception and condensing portion can be kept stable.

Note that a dental plaque detection unit for determining whether or not there is dental plaque on the tooth surface based on the output of the light reception portion may also be included inside of the main body.

Also, in the "specific region" of the bristle raising surface, it is desirable that the bristles are omitted.

With a toothbrush according to an embodiment, the light reception and condensing portion is composed of a Fresnel lens or a diffraction grating lens having a flat outer surface that exists in the specific region of the bristle raising surface and an inner surface that protrudes toward the inner portion of the head portion.

With the toothbrush according to this embodiment, the light reception and condensing portion is composed of a Fresnel lens or a diffraction grating lens having a flat outer surface that exists in the specific region of the bristle raising surface and an inner surface that protrudes toward the inner portion of the head portion. Accordingly, compared to the case of being composed of a simple plano-convex lens, the thickness of the light reception and condensing portion can be set to be thinner in the thickness direction orthogonal to the bristle raising surface. As a result, the thickness of the head portion can be prevented from increasing due to the existence of the light reception and condensing portion.

With a toothbrush according to an embodiment, the light reception portion is arranged in the head portion, and an optical property of the light reception and condensing portion is set such that the radiated light generated by the tooth surface in contact with leading ends of the bristles forms an image on the light reception surface of the light reception portion.

Here, the "optical property of the light reception and condensing portion" indicates the focal length of the lens forming the light reception and condensing portion, for example.

With the toothbrush of this embodiment, the light reception portion is arranged in the head portion. Also, an optical property of the light reception and condensing portion is set such that the radiated light generated by the tooth surface in contact with leading ends of the bristles forms an image on the light reception surface of the light reception portion. Accordingly, the output of the light reception portion further increases. As a result, the accuracy of determining whether or not there is dental plaque on the tooth surface increases.

With a toothbrush according to an embodiment, the light emission portion and the light reception portion are arranged side by side inside of the head portion, the light emission and condensing portion that condenses the light from the light emission portion toward the tooth surface in contact with the leading ends of the bristles is arranged in the specific region, and the light reception and condensing portion and the light emission and condensing portion are composed of the same lens.

With the toothbrush of this embodiment, the light emission portion and the light reception portion are arranged side by side inside of the head portion. Also, the light emission and condensing portion arranged in the specific region condenses the light from the light emission portion toward the tooth surface in contact with the leading ends of the bristles. Accordingly, the intensity of the light emitted to the tooth surface increases. Accordingly, the output of the light reception portion further increases. As a result, the accuracy of determining whether or not there is dental plaque on the tooth surface increases. Also, since the light reception and condensing portion and the light emission and condensing portion are composed of the same lens, it is possible to prevent an increase in the number of components. Accordingly, this toothbrush can be manufactured with a small size and low cost.

With a toothbrush according to an embodiment, a dental plaque detection unit for determining whether or not there is dental plaque on the tooth surface based on the output of the light reception portion is provided inside of the grip portion.

With the toothbrush according to this embodiment, a dental plaque detection unit for determining whether or not there is dental plaque on the tooth surface based on the output of the light reception portion is provided inside of the grip portion. Accordingly, the user can find out the result of determining whether or not there is dental plaque, while brushing his or her teeth. Accordingly, an optical fiber, wire, or the like that extends from the toothbrush to an external device can be omitted. In this kind of case, the user can easily brush his or her teeth without any hindrance when brushing his or her teeth using this toothbrush.

As is evident from the description above, it is possible to keep the light condensing efficiency stable with the toothbrush of this invention.

DETAILED DESCRIPTION

Hereinafter, an embodiment of this invention will be described in detail with reference to the drawings.

Figure 1A:
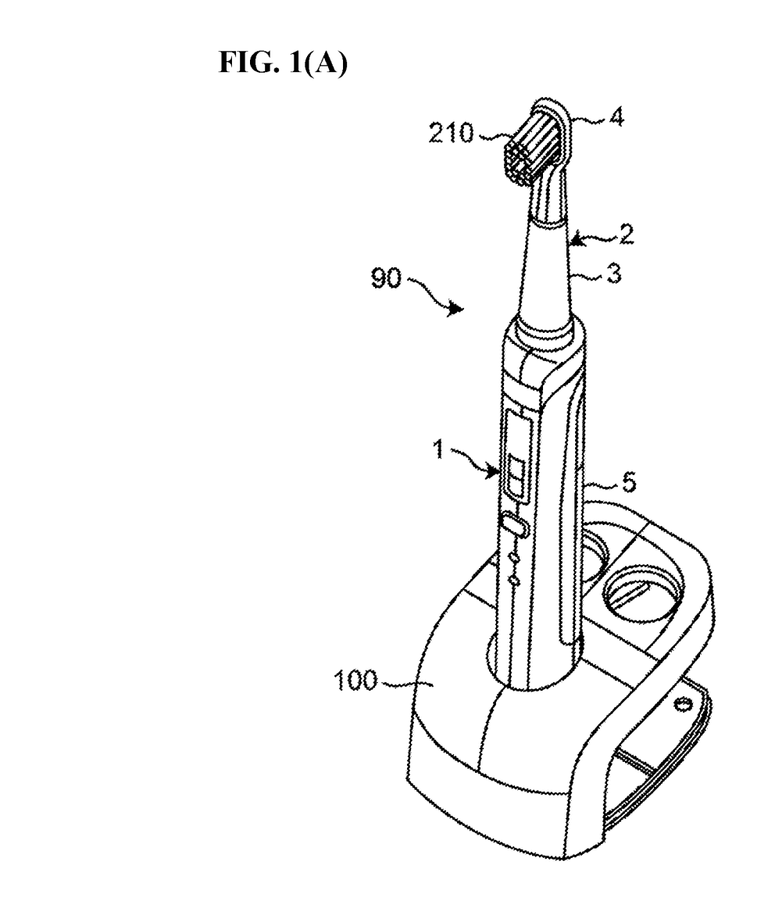
FIG. 1(A) is a diagram showing a perspective view from mutually opposite sides of the exterior of an electric toothbrush of an embodiment, in which a dental plaque detection apparatus of this invention is incorporated.
Figure 1B:
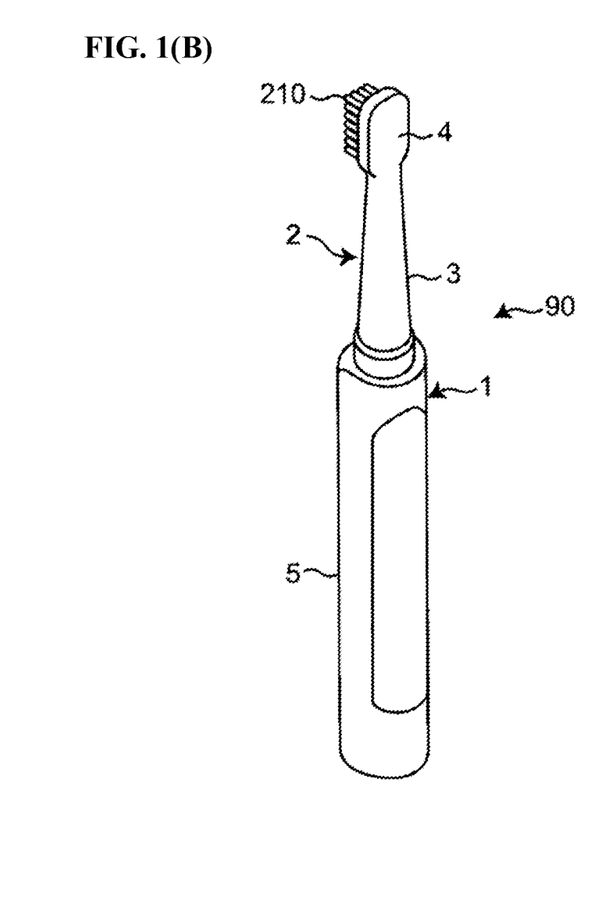
FIG. 1(B) is another diagram showing a perspective view from mutually opposite sides of the exterior of an electric toothbrush of an embodiment, in which a dental plaque detection apparatus of this invention is incorporated.

FIGS. 1(A) and 1(B) show perspective views from mutually opposite directions of the exterior of an electric toothbrush (the entirety of which is indicated by reference numeral 90) of an embodiment, in which a dental plaque detection apparatus of this invention is incorporated. The electric toothbrush 90 includes a head portion 4 on which bristles 210 are provided in a standing manner, a grip portion 5 that is to be gripped with a hand, and a neck portion 3 that joins the head portion 4 and the grip portion 5. The head portion 4 and the neck portion 3 are constituted integrally as a brush member 2, which can be attached to and detached from the grip portion 5. The head portion 4, the neck portion 3, and the grip portion 5 are collectively referred to as a main body 1. The main body 1 has a shape that is elongated in one direction for the sake of convenience when brushing teeth. Note that a charger 100 is illustrated in FIG. 1(A).

Figure 2:
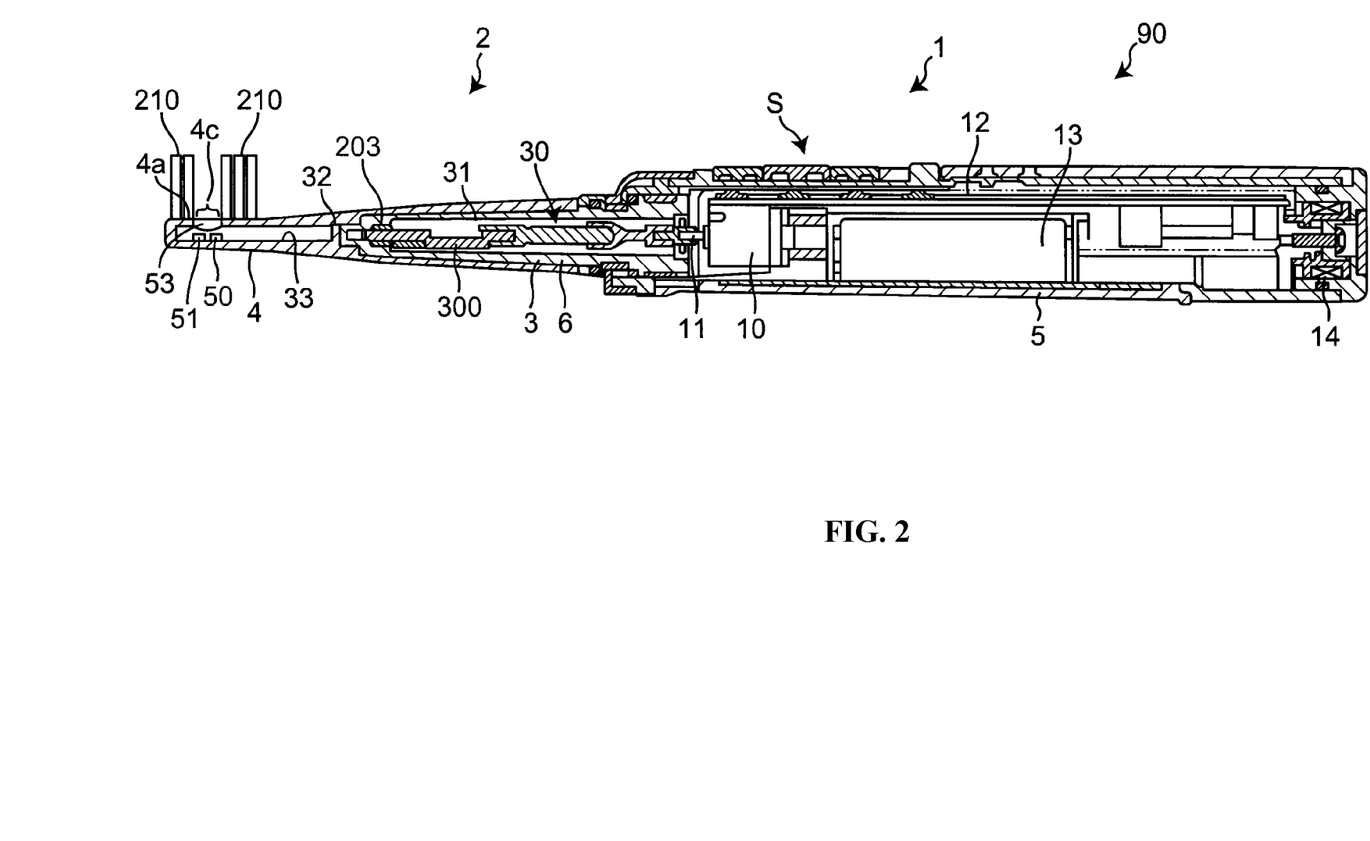
FIG. 2 is a diagram showing a vertical cross section taken when the above-described electric toothbrush is cut along a lengthwise direction.

FIG. 2 shows a vertical cross section taken when the electric toothbrush 90 is cut along a lengthwise direction. The grip portion 5 includes a stem 6 that is provided so as to stick out from the outer housing of the grip portion 5 toward the neck portion 3. The stem 6 has a cylindrical shape with a leading end that is closed. In this example, the neck portion 3 of the brush member 2 is attached by being fit so as to cover the stem 6. Since the brush member 2 is a consumable article, it can be attached to and detached from the grip portion 5 such that it can be replaced with a new article. In this example, the bristles (brush) 210 are provided in a standing manner on a surface (bristle raising surface) 4*a* on one side of the head portion 4 of the brush member 2, so as to protrude about 10 mm to 12 mm from the bristle raising surface 4*a*, through transplantation in this example. Note that the bristles 210 may be welded or adhered instead of being transplanted.

A switch for switching power on and off is provided on the outer surface of the grip portion 5 of the main body 1. Also, a motor 10, which is a drive source, a drive circuit 12, a rechargeable battery 13 serving as a power source portion, a coil 14 for charging, and the like are provided inside of the grip portion 5. When the rechargeable battery 13 is to be charged, contactless charging can be performed through electromagnetic induction by merely placing the main body 1 on the charger 100 shown in FIG. 1(A).

As shown in FIG. 2, a bearing 203 is provided inside of the stem 6. The leading end of an eccentric shaft 30 coupled to a rotary shaft 11 of the motor 10 is inserted into the bearing 203. The eccentric shaft 30 has a weight 300 near the bearing 203, and the center of gravity of the eccentric shaft 30 is shifted from the rotary center. When the drive circuit 12 supplies a drive signal (e.g., a pulse width modulation signal) corresponding to the operation mode to the motor 10 and the rotary shaft 11 of the motor 10 is rotated, the eccentric shaft 30 also rotates accompanying the rotation of the rotary shaft 11. The eccentric shaft 30 performs the action of pivoting about the rotational center since its center of gravity is shifted from the rotational center. Accordingly, the leading end of the eccentric shaft 30 repeatedly collides with the inner surface of the bearing 203, causing the bristles 210 to vibrate (move) at a high speed.

In a specific region 4*c* in the approximate center of the bristle raising surface 4*a* of the head portion 4, the bristles are omitted. The light emission portion 50 and the light reception portion 51 are arranged side by side inside of the head portion 4, corresponding to the specific region 4*c*. The light condensing portion 53 serving as the light reception and condensing portion and the light emission and condensing portion is arranged in the housing portion (outer housing) forming the specific region 4*c* of the head portion 4.

Figure 4:
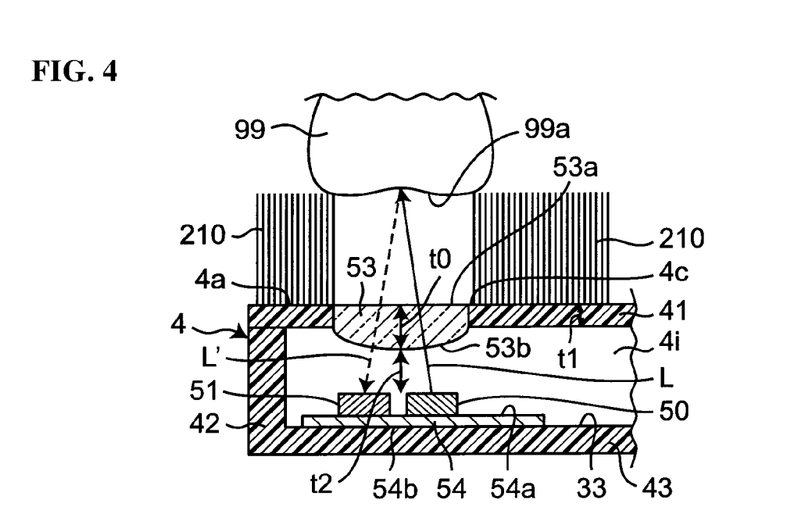
FIG. 4 is a diagram showing a cross-sectional structure of a head portion of the above-described electric toothbrush.

As shown in FIG. 4, the outer housing of the head portion 4 includes a flat outer wall 41 that includes the bristle raising surface 4*a*, a flat rear surface wall 43 that opposes the outer wall 41, and a peripheral wall 42 that connects the peripheral edge portions of the outer wall 41 and the rear surface wall 43, and the outer housing is integrally formed in a box shape having a hermetically-sealed internal space 4*i*. The outer wall, the rear surface wall 43, and the peripheral wall 42 are composed of a resin material with a thickness of about t1=1 mm to 3 mm.

The light emission portion 50 and the light reception portion 51 are attached to the inner surface of the rear surface wall 43 via a flat plate-shaped wiring substrate 54. The wiring substrate 54 includes wires (not shown) that are electrically connected to the light emission portion 50 and the light reception portion 51, on one surface 54*a* to which the light emission portion 50 and the light reception portion 51 are attached, and a surface 54*b* on the side opposite to the surface 54*a*. These wires are electrically connected to the drive circuit 12 via a wire 33 provided on the inner surface of the rear surface wall 43, a wire 32 provided penetrating through the outer housing of the head portion 4 shown in FIG. 2, and a wire 31 provided on the stem 6.

The light emission portion 50 shown in FIG. 4 includes a light emitting diode that emits light L having a peak wavelength that corresponds to ultraviolet or blue to the tooth surface 99*a* through the light condensing portion 53 of the specific region 4*c*. In this example, the light emitting diode is an LED (model number SM0603UV-405) manufactured by Bivar Corp., and generates light L having a peak wavelength of 405 nm.

The light reception portion 51 includes a photodiode that receives radiated light L' from the tooth surface 99*a* resulting from the light L, through the light condensing portion 53 of the specific region 4*c*, and outputs a signal corresponding to the intensity of the radiated light L'. In this example, the photodiode is composed of a PD (Photo Diode) (model number NJL6401R-3) manufactured by New Japan Radio Co., Ltd. Note that the light reception portion 51 need not be a photodiode and may be a phototransistor.

In this example, the light condensing portion 53 is composed of a plano-convex lens that has a flat outer surface 53*a* that exists in a specific region 4*c* of the bristle raising surface 4*a* and an inner surface 53*b* that protrudes toward the internal space 4*i* of the head portion 4. The plano-convex lens is held by being fit into a through hole provided in the outer wall 41 of the head portion 4. In this example, the outer surface 53*a* of the plano-convex lens is flush with the bristle raising surface 4*a*. As a result, the entire bristle raising surface 4*a* of the head portion 4 is flat. That is, the bristle raising surface 4*a* is flat overall, including the specific region 4*c* and the region holding and surrounding the bristles 210 on the bristle raising surface 4*a*. Note that the bristle raising surface 4*a* need not be entirely flat, and a region that is larger than the specific region 4*c* and influences the light condensing efficiency of the light condensing portion 53 need only be flat.

In this example, the diameter of the plano-convex lens forming the light condensing portion 53 is set to 3 mm, its thickness t0 is set to 2 mm, its refractivity is set to 1.59, and its material is set to polycarbonate. Also, the distance t2 between the plano-convex lens and the light emission portion 50 and light reception portion 51 is set to 2 mm.

The light condensing portion 53 functions as a light emission and condensing portion to condense the light L from the light emission portion 50 to the tooth surface 99*a* that is in contact with the leading ends of the bristles 210, and functions as a light reception and condensing portion to condense the radiated light L' from the tooth surface 99*a* to the light reception surface of the light reception portion 51. Accordingly, the intensity of the light L emitted to the tooth surface 99*a* increases, and the intensity of the radiated light L' on the light reception surface increases. Accordingly, the output of the light reception portion 51 further increases. Also, since the light emission and condensing portion and the light reception and condensing portion are composed of the same lens, it is possible to prevent an increase in the number of members. Accordingly, this toothbrush can be manufactured with a small size and low cost.

Figure 3:
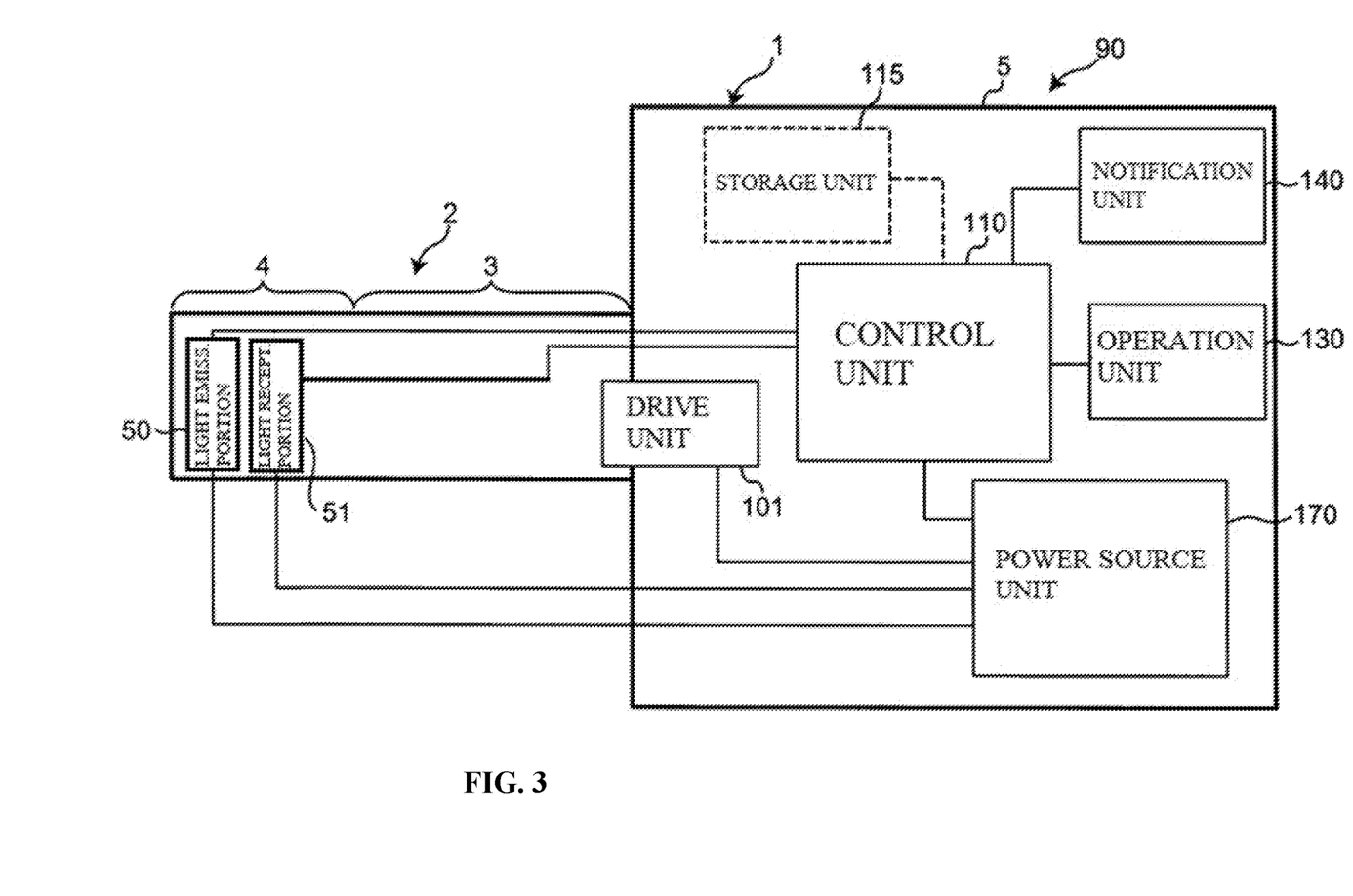
FIG. 3 is a diagram showing a block configuration of a control system of the above-described electric toothbrush.

FIG. 3 shows a block configuration of a control system of the electric toothbrush 90. A control unit 110, a storage unit 115, an operation unit 130, a notification unit 140, and a power source unit 170, which form the above-described drive circuit 12, are included inside of the grip portion 5 of the electric toothbrush 90. Note that the drive portion 101 indicates the above-described motor 10, rotary shaft 11, eccentric shaft 30, bearing 203, and weight 300.

The control unit 110 includes a CPU (Central Processing Unit) that operates according to software, and executes driving of the motor 10, as well as processing for identifying whether or not there is dental plaque (or dental calculus) on the tooth surface 99a, and other types of processing.

The operation unit 130 includes the above-described switch S and functions so that the user switches on and off the power source of the electric toothbrush 90.

In this example, the storage unit 115 includes an EEPROM (Electrically Erasable Read-Only Memory) that can non-temporarily store data. A control program for controlling the control unit 110 is stored in the storage unit 115.

The notification unit 140 includes a buzzer in this example, and performs notification of whether or not there is dental plaque (or dental calculus) by sounding a buzzer sound. Note that instead of or in addition to the buzzer, the notification unit 140 may include an LED lamp, and may perform notification of whether or not there is dental plaque (or dental calculus) through illumination or blinking of the LED lamp.

The power source unit 170 includes the above-described rechargeable battery 13, and supplies power (in this example, DC 2.4 V) to the units in the electric toothbrush 90.

With this electric toothbrush 90, when the user switches on the switch S, the control unit 110 causes the bristles 210 to rapidly vibrate (move) by rotating the motor 10. Furthermore, as will be described next, the control unit 110 functions as a dental plaque detection unit to execute processing for determining whether or not there is dental plaque (or dental calculus) on the tooth surface 99a.

Specifically, as shown in FIG. 4, the control unit 110 turns on the light emission portion 50 and emits the light L from the light emission portion 50 to the tooth surface 99a through the light condensing portion 53 of the specific region 4c. In response, the radiated light L' is radiated from the tooth surface 99a. The radiated light L' passes through the light condensing portion 53 of the specific region 4c and is received by the light reception portion 51. The output of the light reception portion 51 is input to the control unit 110.

Next, based on the output of the light reception portion, the control unit 110 determines whether or not there is dental plaque on the tooth surface 99a using a known procedure for detecting fluorescent light that is unique to dental plaque, as disclosed in Patent Document 2 (JP 2002-522102A), for example. Here, with this toothbrush, the light condensing portion 53 arranged in the housing portion of the specific region 4c functions as the light emission and condensing portion to condense the light L from the light emission portion 50 toward the tooth surface 99a that is in contact with the leading ends of the bristles 210, and functions as a light reception and condensing portion to condense the radiated light L' from the tooth surface 99a toward the light reception surface of the light reception portion 51. Accordingly, the output of the light reception portion 51 increases, and as a result, it is possible to increase the accuracy of determining whether or not there is dental plaque on the tooth surface 99a.

Moreover, with this electric toothbrush 90, the entirety of the bristle raising surface 4a of the head portion 4 is flat. For this reason, at the time of use, water droplets are not likely to attach to the light condensing portion 53 and its periphery. Accordingly, the light condensing efficiency of the light condensing portion 53 can be kept stable.

Thereafter, in this example, the control unit 110 performs notification of whether or not there is dental plaque (or dental calculus) by sounding the buzzer sound using the notification unit 140.

Accordingly, the user can find out the result of determining whether or not there is dental plaque (or dental calculus), while brushing his or her teeth. Accordingly, an optical fiber, wire, or the like that extends from the electric toothbrush 90 to an external device can be omitted. In this kind of case, the user can easily brush his or her teeth without any hindrance when brushing his or her teeth using this electric toothbrush 90.

MODIFIED EXAMPLE 1

Figure 5A:
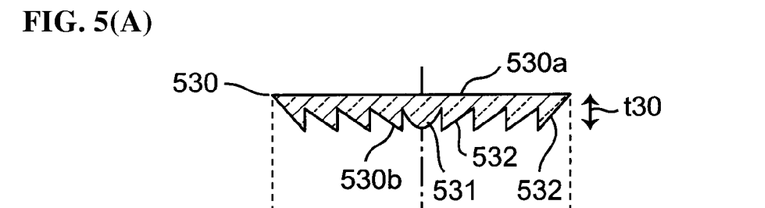
FIG. 5(A) is a diagram showing a cross section of a Fresnel lens constituting a light condensing portion.
Figure 5B:
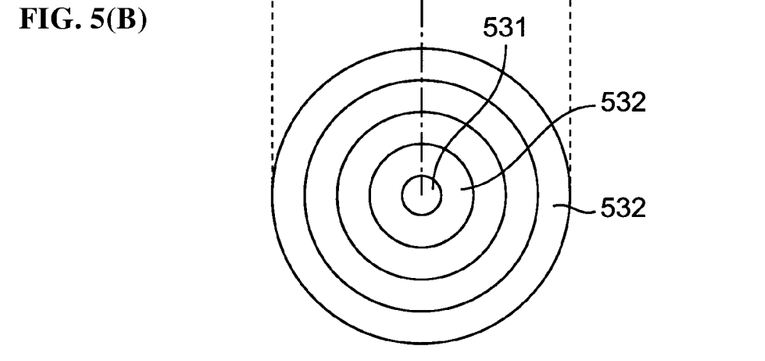
FIG. 5(B) is a diagram showing a view from below of the Fresnel lens in FIG. 5(A).

In the above example, the light condensing portion 53 is composed of a plano-convex lens, but there is no limitation to this. For example, as shown in FIGS. 5(A) and 5(B), the light condensing portion 53 may be composed of a Fresnel lens 530. FIG. 5(A) shows a cross-section corresponding to FIG. 4 of the Fresnel lens 530. FIG. 5(B) shows a view from below of the Fresnel lens 530 in FIG. 5(A).

The Fresnel lens 530 includes a flat outer surface 530a that exists in the specific region 4c of the bristle raising surface 4a, and an inner surface 530b that protrudes toward the inner space 4i of the head portion 4. The inner surface 530b includes a central portion 531 that protrudes in a curved manner, and multiple ring-shaped portions 532, 532, . . . that wrap around the central portion 531 and protrude in the form of sawteeth in cross-section. The inclinations of the protrusions of the ring-shaped portions 532, 532, . . . are the same.

In this example, the diameter of the Fresnel lens 530 is set to 3 mm, its thickness t30 is set to 0.3 mm, its refractivity is set to 1.59, and its material is set to polycarbonate.

With the Fresnel lens 530, the thickness of the light condensing portion 53 is set to be thinner in the thickness direction orthogonal to the bristle raising surface 4a, compared to the case of being composed of a simple plano-convex lens. As a result, it is possible to suppress a case in which the thickness of the head portion 4 increases due to the presence of the light condensing portion 53.

MODIFIED EXAMPLE 2

Figure 6A:
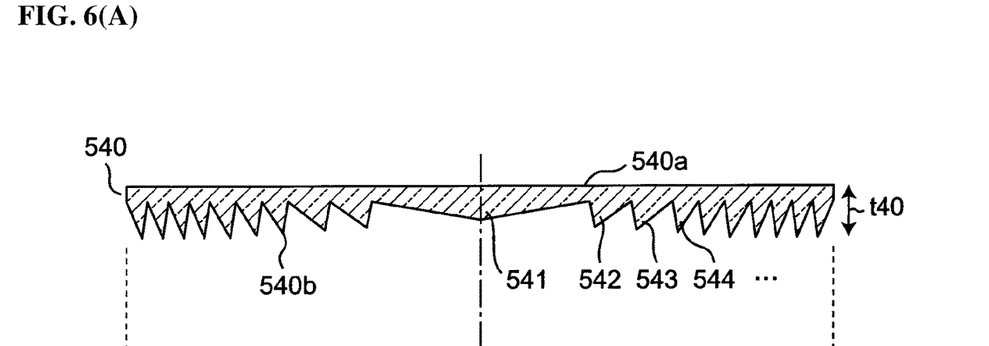
FIG. 6(A) is a diagram showing a cross section of a diffraction grating lens constituting a light condensing portion.
Figure 6B:
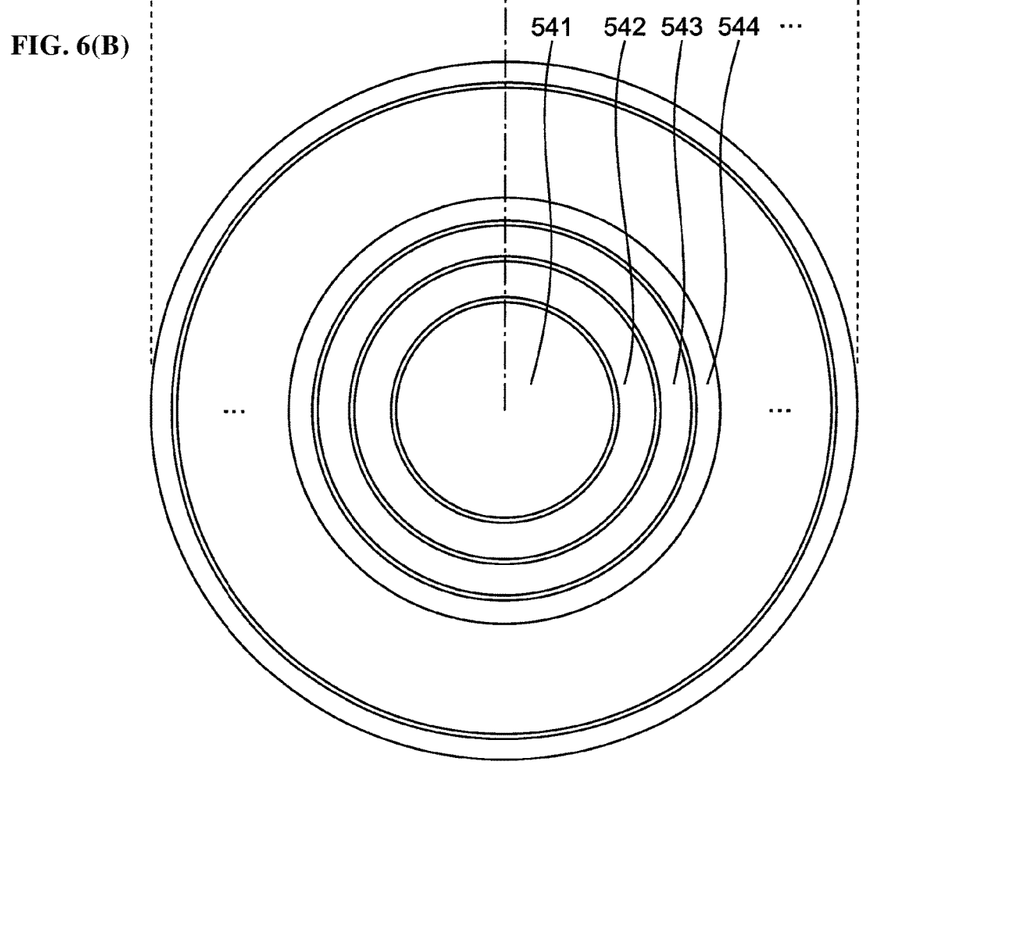
FIG. 6(B) is a diagram showing a view from below of the diffraction grating lens in FIG. 6(A).

Also, as shown in FIGS. 6(A) and 6(B), the light condensing portion 53 may be composed of a diffraction grating lens 540. FIG. 6(A) shows a cross-section corresponding to FIG. 4 of the diffraction grating lens 540. FIG. 6(B) shows a view from below of the diffraction grating lens 540 in FIG. 6(A).

The diffraction grating lens 540 includes a flat outer surface 540a that exists in the specific region 4c of the bristle raising surface 4a, and an inner surface 540b that protrudes toward the inner space 4i of the head portion 4. The inner surface 540b includes a central portion 541 that protrudes in a circular cone shape, and multiple ring-shaped portions 542, 543, 544, . . . that wrap around the central portion 541 and protrude in the form of sawteeth in cross-section. The pitch between the protrusions of the ring-shaped portions 542, 543, 544, . . . decreases toward the outer side in the radial direction, and thus the protrusions are sharper the closer the ring-shaped portion is to the outer side.

With this diffraction grating lens 540, similarly to that case of the Fresnel lens 530, the thickness of the light condensing portion 53 can be set to be thinner in the thickness direction orthogonal to the bristle raising surface 4a, compared to the case of being composed of a simple plano-convex lens. As a result, it is possible to suppress a case in which the thickness of the head portion 4 increases due to the presence of the light condensing portion 53.

MODIFIED EXAMPLE 3

Figure 7:
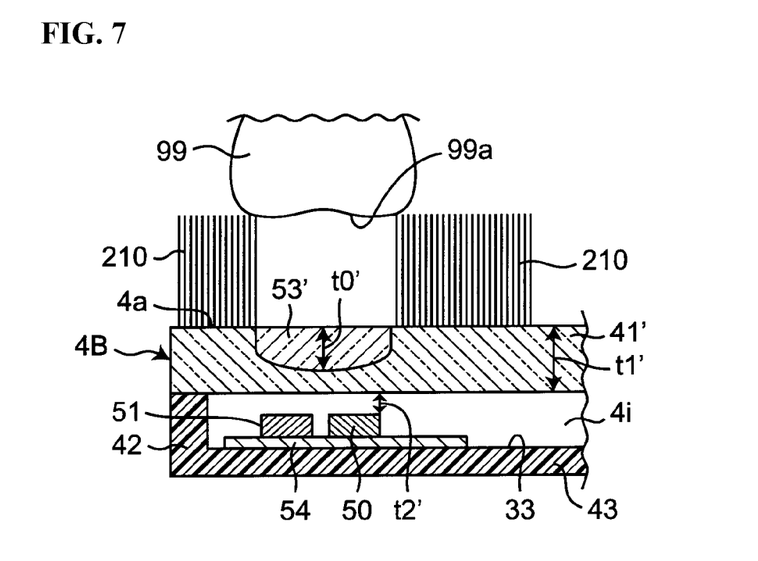
FIG. 7 is a diagram showing a modified example in which a plano-convex lens forming a light condensing portion is embedded in an outer surface of an outer wall of the head portion.

In the above-described example of FIG. 4, the plano-convex lens forming the light condensing portion 53 is held by being fit into a through hole provided in the outer wall 41 of the hole portion 4. However, there is no limitation to this. For example, as shown in FIG. 7, the outer wall 41' of the head portion (indicated by reference numeral 4B) may be constituted by transparent resin, and a plano-convex lens may be embedded as the light condensing portion 53' in the outer surface (i.e., the bristle raising surface 4a) of the outer wall 41'. In this example, the flat outer surface of the plano-convex lens forming the light condensing portion 53' is flush with the bristle raising surface 4a, similarly to the example shown in FIG. 4. The convex surface side of the plano-convex lens is embedded in the outer wall 41'. Note that in FIG. 7, constituent elements that correspond to the constituent elements in FIG. 4 are denoted by the same reference numerals thereas (the same follows for later-described FIGS. 8 to 11).

According to this configuration, the bristle raising surface 4a is flat overall, including the specific region 4c and the region holding and surrounding the bristles 210 on the bristle raising surface 4a. Accordingly, similarly to the example of FIG. 4, during use, water droplets are not likely to attach to the light condensing portion 53' and its periphery. Accordingly, the light condensing efficiency of the light condensing portion 53' can be kept stable. Moreover, it is possible to more strongly hold the plano-convex lens serving as the light condensing portion 53'.

MODIFIED EXAMPLE 4

Figure 8:
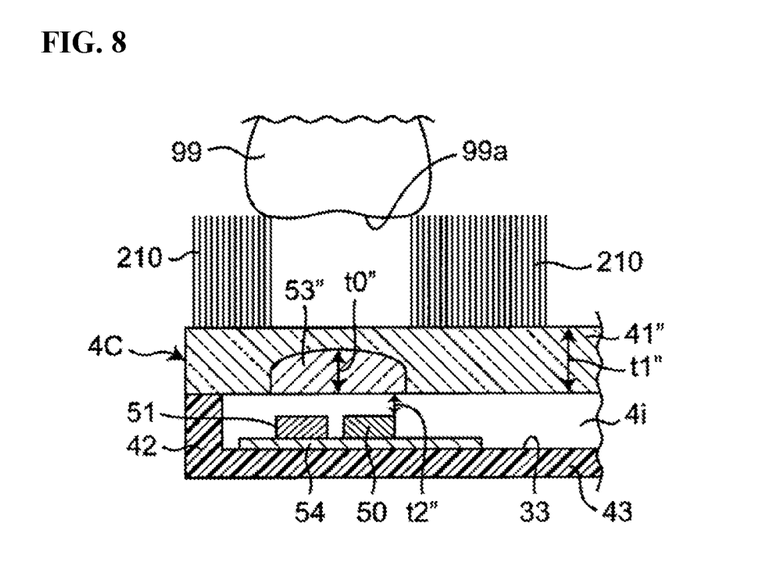
FIG. 8 is a diagram showing another modified example in which a plano-convex lens forming a light condensing portion is embedded in an inner surface of an outer wall of the head portion.

Similarly, as shown in FIG. 8, the outer wall 41" of the head portion (indicated by reference numeral 4C) may be constituted by transparent resin, and the plano-convex lens may be embedded as the light condensing portion 53" in the inner surface of the outer wall 41". In this example, unlike the example in FIG. 7, the flat surface of the plano-convex lens forming the light condensing portion 53" is flush with the inner surface of the outer wall 41". The convex surface side of the plano-convex lens is embedded in the outer wall 41".

In this configuration as well, the bristle raising surface 4a is flat overall, including the specific region 4c and the region holding and surrounding the bristles 210 on the bristle raising surface 4a. Accordingly, similarly to the example of FIG. 4, during use, water droplets are not likely to attach to the light condensing portion 53" and its periphery. Accordingly, the light condensing efficiency of the light condensing portion 53" can be kept stable. Moreover, it is possible to more strongly hold the plano-convex lens serving as the light condensing portion 53".

Figure 9A:
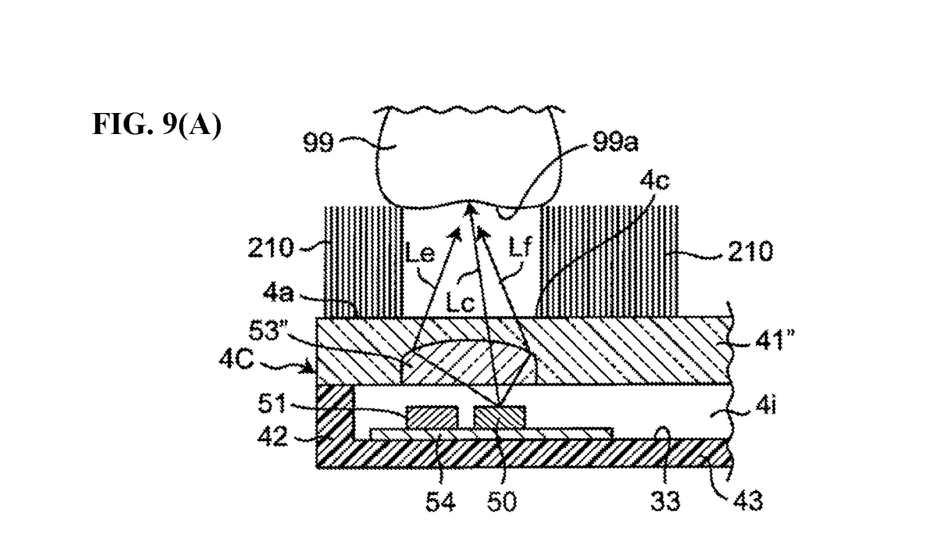
FIG. 9(A) is a diagram illustrating a function of the light condensing portion in the configuration of FIG. 8.
Figure 9B:
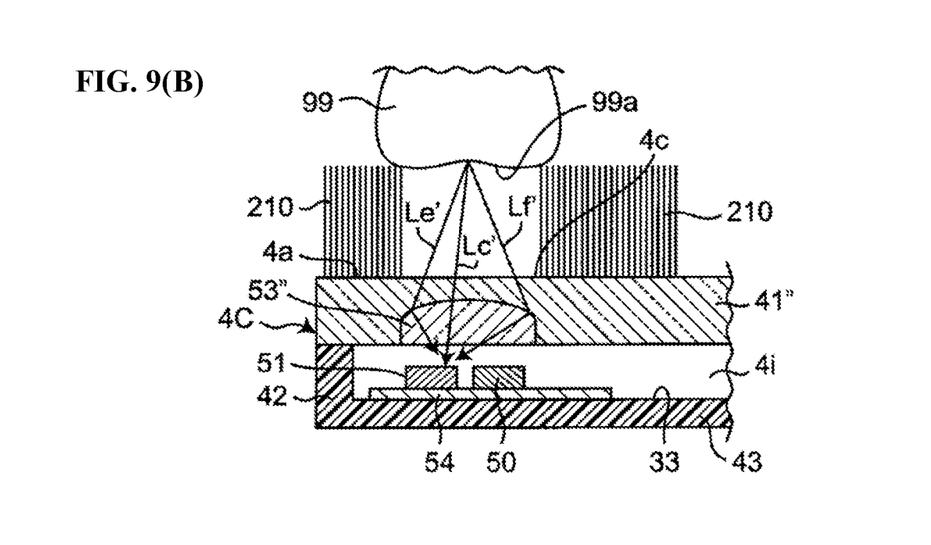
FIG. 9(B) is a diagram illustrating a function of the light condensing portion in the configuration of FIG. 8.

Also, with the configuration of FIG. 8, as shown in FIG. 9(A), in a state in which the tooth surface 99a is in contact with the leading ends of the bristles 210, the light L generated by the light emission portion 50 is set to form an image on the tooth surface 99a through an optical property (e.g., the focal distance) of the light condensing portion 53". FIG. 9(A) shows the path of the light Lc that passes through the vicinity of the center of the lens in the light L generated by the light emission portion 50 and the paths of the lights Le and Lf that pass through the vicinity of the circumferential edge of the lens in the light L generated by the light emission portion 50. Also, as shown in FIG. 9(B), in a state in which the tooth surface 99a is in contact with the leading ends of the bristles 210, the radiated light L' emitted by the tooth surface 99a is set to form an image on the light reception surface of the light reception portion 51 due to an optical property (in particular, the focal length) of the light condensing portion 53". FIG. 9(B) shows the path of light Lc' that passes through the vicinity of the center of the lens of the radiated light L' emitted by the tooth surface 99a and the paths of the lights Le' and Lf' that pass through the vicinity of the circumferential edge of the lens of the radiated light L' emitted by the tooth surface 99a.

If the optical property of the light condensing portion 53" is set in this way, the output of the light reception portion 51 further increases. As a result, it is possible to increase the efficiency of determining whether or not there is dental plaque on the tooth surface 99a. This circumstance is similar in the above-described examples of FIGS. 4 and 7.

MODIFIED EXAMPLE 5

In the above-described example of FIG. 4, the outer housing of the head portion 4 is constituted integrally in the form of a box. However, there is no limitation to this. For example, as shown in FIG. 10, the head portion (indicated by reference numeral 4D) may be constituted by an inner box portion 4D2 that is formed by extending the stem 6 shown in FIG. 4, and an outer tube portion 4D1 that is detachably fit onto the outside of the inner box portion 4D2.

In this example, the inner box portion 4D2 is composed of a resin material, includes a flat outer wall 46, a flat rear surface wall 48 opposing the outer wall 46, and a peripheral wall 47 that connects the peripheral edge portions of the outer wall 46 and the rear surface wall 48, and is constituted integrally in the form of a box having a hermetically-sealed inner space 45i. Similarly to the inner space 45i in the head portion 4 in FIG. 4, a wire 33 that electrically connects the light emission portion 50, the light reception portion 51, the wiring substrate 54, and the drive circuit 12 is arranged in the inner space 45i of the inner box portion 4D2. Also, a first light condensing portion 56 is arranged in the portion of the outer wall 46 of the inner box portion 4D2 that opposes the light emission portion 50 and the light reception portion 51.

In this example, the first light condensing portion 56 is composed of a plano-convex lens having a flat outer surface 56a and an inner surface 56b that protrudes toward the inner space 45i of the inner box portion 4D2. The plano-convex lens is held by being fit into a through hole provided in the outer wall 46. In this example, the outer surface 56a of the plano-convex lens is flush with the outer surface of the outer wall 46. As a result, it is easy to attach and detach the outer tube portion 4D1 by fitting it onto the outside of the inner box portion 4D2.

Figure 10:
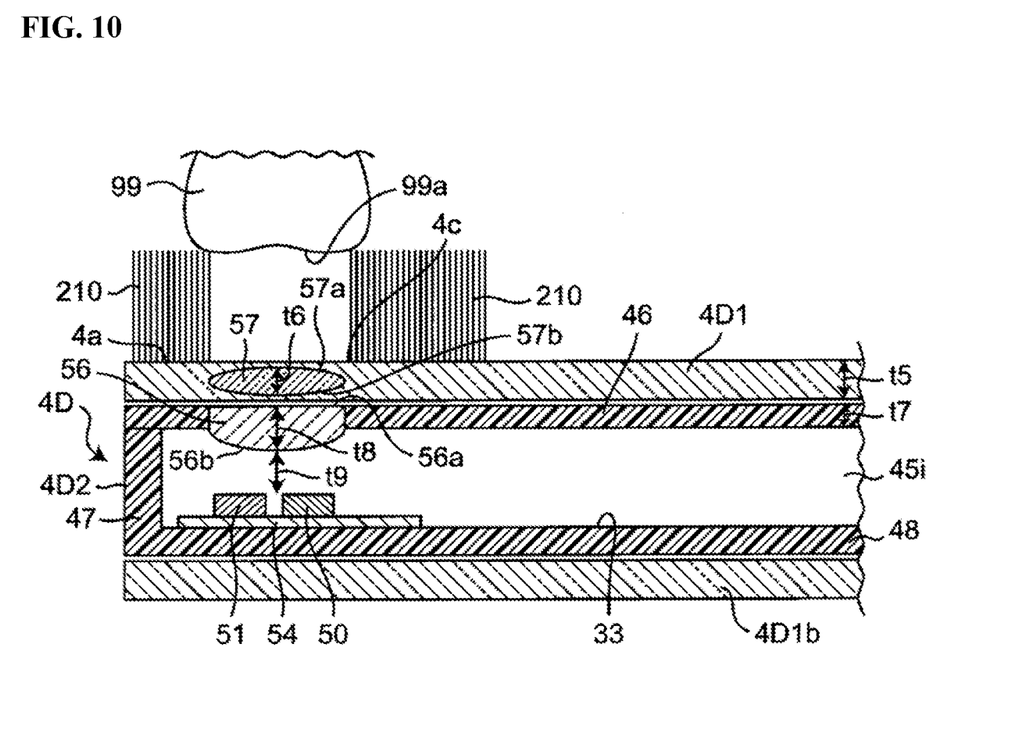
FIG. 10 is a diagram showing an example in which the head portion of the electric toothbrush is composed of a combination of two members.

The outer tube portion 4D1 is composed of a transparent resin material and is formed into a rectangular tube shape so as to be able to slide and fit onto the outside of the inner box portion 4D2 in a lateral direction in FIG. 10. On the outer circumferential surface of the outer tube portion 4D1, bristles (a brush) 210 are provided in a standing manner through bristle transplantation in this example on a surface (bristle raising surface) 4a on one side corresponding to the outer wall 46 of the inner box portion 4D2.

In a specific region 4c in the approximate center of the bristle raising surface 4a of the outer tube portion 4D1, the bristles are omitted. A second light condensing portion 57 is arranged at the portion (inside the wall) of the outer tube portion 4D1 corresponding to the specific region 4c.

The second light condensing portion 57 is composed of a biconvex lens that has an outer surface 57a that protrudes toward the outside (toward the tooth surface 99a) and an inner surface 57b that protrudes toward the inside (toward the inner box portion 4D2). The biconvex lens is held by being embedded in a wall of the outer tube portion 4D1.

With the configuration of FIG. 10, the light L emitted by the light emission portion 50 passes through the two light condensing portions, namely the first light condensing portion 56 and the second light condensing portion 57, and is condensed toward the tooth surface 99a. Also, the radiated light L' radiated from the tooth surface 99a passes through the two light condensing portions, namely the second light condensing portion 57 and the first light condensing portion 56, and is condensed toward the light reception surface of the light reception portion 51. Accordingly, the output of the light reception portion 51 further increases. As a result, it is possible to increase the efficiency of determining whether or not there is dental plaque on the tooth surface 99a.

Also, the bristle raising surface 4a of the outer tube portion 4D1 is flat overall, including the specific region 4c and the region of the bristle raising surface 4a holding and surrounding the bristles 210. Accordingly, similarly to the example of FIG. 4, during use, water droplets are not likely to attach to the second light condensing portion 57 and its periphery. Accordingly, the light condensing efficiency of the second light condensing portion 57 can be kept stable.

Note that at least one of the first light condensing portion 56 and the second light condensing portion 57 may be omitted.

MODIFIED EXAMPLE 6

Figure 11:
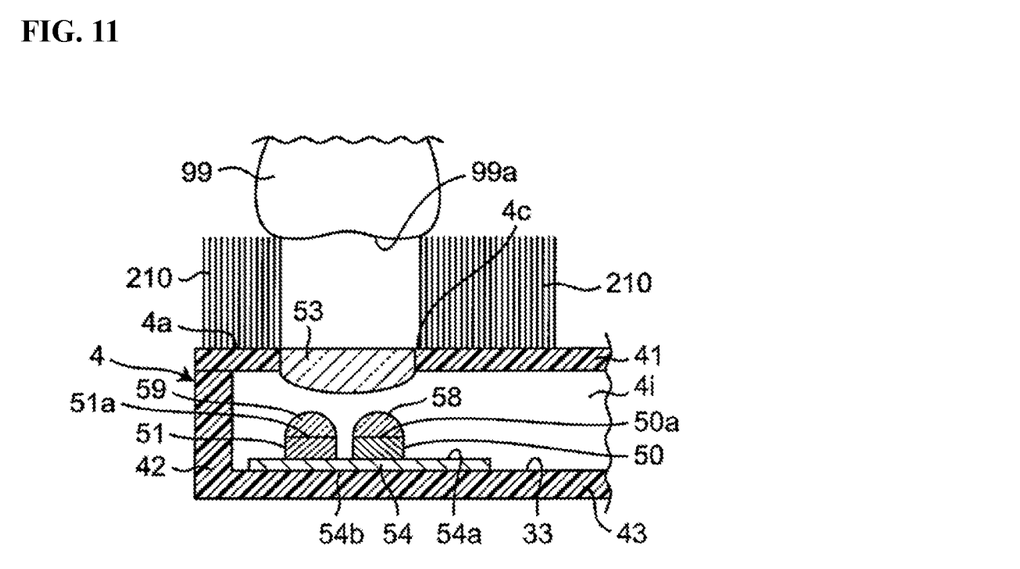
FIG. 11 is a diagram showing an example in which a light condensing function is obtained by providing the upper surfaces of the light emission portion and the light reception portion with approximately hemispherical transparent resin.

In the above-described examples, the light condensing portions 53, 53', 53", . . . are arranged in the housing portion forming the specific region 4c of the head portion 4. However, there is no limitation to this. For example, as shown in FIG. 11 (corresponds to FIG. 4), approximately hemispherical transparent resins 58 and 59 may be provided on the upper surfaces (surfaces on the side opposing the light condensing portion 53) of the light emission portion 50 and the light reception portion 51 to provide a light condensing function.

According to this configuration, the output of the light reception portion 51 further increases. As a result, it is possible to increase the efficiency of determining whether or not there is dental plaque on the tooth surface 99a.

In the above-described embodiment, the light emission portion 50 and the light reception portion 51 are arranged inside of the head portion 4, but there is no limitation to this. The light emission portion 50 and the light reception portion 51 may be provided inside of the main body 1. For example, the light emitting diode forming the light emission portion 50 and the photodiode forming the light reception portion 51 may be arranged inside of the grip portion 5, and a waveguide composed of an optical fiber may be provided between the light emitting diode and photodiode and the light condensing portion 53.

In this example, an electric toothbrush was described, but there is no limitation thereto. The present invention can also be applied to a manual toothbrush.

The foregoing embodiments are exemplary and various modifications are possible without departing from the scope of the present invention. The above-described multiple embodiments can be achieved independently or in combination with each other. Also, various features in different embodiments can be achieved independently, and features in different embodiments can be combined.

The invention claimed is:

1. A toothbrush, comprising:
a main body including a head portion with a bristle raising surface on which bristles are provided in a standing manner, a grip portion to be gripped with a hand, and a neck portion that joins the head portion and the grip portion,
a light emission portion configured to emit light through a specific region of the bristle raising surface toward a tooth surface, and a light reception portion configured to receive radiated light from the tooth surface resulting from the light, through the specific region, being included inside of the main body,
wherein it is determined whether or not there is dental plaque on the tooth surface based on an output of the light reception portion,
a light reception and condensing portion including a lens configured to condense the radiated light from the tooth surface toward a light reception surface of the light reception portion is arranged in a housing portion forming the specific region, and
a flat region of the bristle raising surface of the head portion that includes the specific region and is larger than the specific region.

2. The toothbrush according to claim 1, wherein the light reception and condensing portion are composed of a Fresnel lens or a diffraction grating lens having a flat outer surface that exists in the specific region of the bristle raising surface and an inner surface that protrudes toward the inner portion of the head portion.

3. The toothbrush according to claim 1, wherein the light reception portion is arranged in the head portion, and
an optical property of the light reception and condensing portion is set such that the radiated light generated by the tooth surface in contact with leading ends of the bristles forms an image on the light reception surface of the light reception portion.

4. The toothbrush according to claim 1, wherein the light emission portion and the light reception portion are arranged side by side inside of the head portion,
the light emission and condensing portion that condenses the light from the light emission portion toward the tooth surface in contact with the leading ends of the bristles is arranged in the specific region, and
the light reception and condensing portion and the light emission and condensing portion are composed of the same lens.

5. The toothbrush according to claim 1, wherein a dental plaque detection unit for determining whether or not there is dental plaque on the tooth surface based on the output of the light reception portion is provided inside of the grip portion.

* * * * *